United States Patent [19]

Teraji et al.

[11] Patent Number: 4,585,762
[45] Date of Patent: Apr. 29, 1986

[54] PHOSPHOLIPID DERIVATIVES, PROCESSES FOR USE THEREOF AND PHARMACEUTICAL COMPOSITION OF THE SAME

[75] Inventors: Tsutomu Teraji, Osaka; Eishiro Todo; Norihiko Shimazaki, both of Toyonaka; Teruo Oku, Osaka; Takayuki Namiki, Minoo, all of Japan

[73] Assignee: Fujisawa Pharmaceutical Co., Ltd., Osaka, Japan

[21] Appl. No.: 513,451

[22] Filed: Jul. 13, 1983

[30] Foreign Application Priority Data

Jul. 30, 1982 [GB] United Kingdom ................ 8222020

[51] Int. Cl.⁴ .................... A61K 31/66; C07F 9/09
[52] U.S. Cl. .................... 514/129; 558/172; 558/184; 558/186; 558/194; 558/214
[58] Field of Search ............ 260/953; 424/217; 514/129

[56] References Cited

FOREIGN PATENT DOCUMENTS 2659048 7/1978 Fed. Rep. of Germany .
2287901 5/1976 France .

OTHER PUBLICATIONS

Joo et al, "Index Chemicus", vol. 30, #12, 9/16/68, #100906.

Malkin, "Chemistry & Industry," vol. 19, (1961) pp. 605–611.

Primary Examiner—Anton H. Sutto
Attorney, Agent, or Firm—Oblon, Fisher, Spivak, McClelland & Maier

[57] ABSTRACT

New phospholipid derivatives represented by the formula:

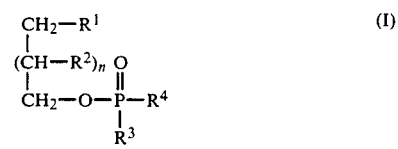

wherein
$R^1$ is alkyl, alkoxy, alkylthio or alkylsulfonyl;
$R^2$ is hydrogen, hydroxy, alkoxy, lower alkanoyloxy or lower alkylcarbamoyloxy;
$n$ is 0 or 1;
$R^3$ is hydroxy or protected hydroxy; and
$R^4$ is lower alkoxy or lower alicyclic-oxy group which is substituted with 2 or more hydroxy or protected hydroxy groups, and may be substituted with lower alkoxy or another alicyclic-oxy group having two or more hydroxy or protected hydroxy groups, in which the alicyclic ring may contain an oxygen atom;

and pharmaceutically acceptable salt thereof, which exhibit antitumor activity.

10 Claims, No Drawings

PHOSPHOLIPID DERIVATIVES, PROCESSES FOR USE THEREOF AND PHARMACEUTICAL COMPOSITION OF THE SAME

This invention relates to phospholipid derivatives. More particularly, it relates to new phospholipid derivatives which have antitumor activity, to processes for the preparation thereof, and to pharmaceutical composition comprising the same for therapeutic treatment of cancer.

Accordingly, one object of this invention is to provide new and useful phospholipid derivatives.

Another object of this invention is to provide processes for preparation of the phospholipid derivatives.

A further object of this invention is to provide useful pharmaceutical compositions comprising said phospholipid derivatives as an antitumor agent.

Still further object of the present invention is to provide a therapeutic method of treating cancer.

The object phospholipid derivatives of the present invention are novel and include the compound of the formula (I):

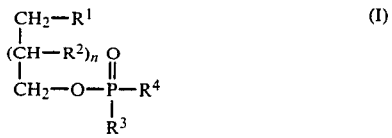

wherein
$R^1$ is alkyl, alkoxy, alkylthio or alkylsulfonyl;
$R^2$ is hydrogen, hydroxy, alkoxy, lower alkanoyloxy or lower alkylcarbamoyloxy;
n is 0 or 1;
$R^3$ is hydroxy or protected hydroxy; and
$R^4$ is lower alkoxy or lower alicyclic-oxy group which is substituted with 2 or more hydroxy or protected hydroxy groups, and may be substituted with lower alkoxy or another alicyclic-oxy group having two or more hydroxy or protected hydroxy groups, in which the alicyclic ring may contain an oxygen atom;
and pharmaceutically acceptable salt thereof.

In the above and subsequent description of the present specification, suitable examples and illustrations of the various definitions to be included within the scope of the invention are explained in details as follows.

The term "lower" is intended to mean 1 to 6 carbon atom(s) and the term "higher" is intended to mean 7 to 25 carbon atoms, unless otherwise indicated.

Suitable "alkyl" for $R^1$ is straight or branched one containing 1 to 25 carbon atoms and may include methyl, ethyl, propyl, isopropyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl and the like, and preferably the higher ones.

Suitable "alkoxy" for $R^1$ may include alkyl-O-groups wherein the alkyl moiety is the same as defined above, and preferably the higher ones.

Suitable "alkylthio" for $R^1$ may include alkyl-S-groups wherein the alkyl moiety is the same as defined above, and preferably the higher ones.

Suitable "alkylsulfonyl" for $R^1$ may include alkyl-$SO_2$-groups wherein the alkyl moiety is the same as defined above and preferably the higher ones.

Suitable "alkoxy" for $R^2$ is the same as the aforementioned alkoxy for $R^1$, and preferably the ones containing 1 to 20 carbon atoms.

Suitable "lower alkanoyl" moiety in the "lower alkanoyloxy" for $R^2$ is straight or branched one containing 1 to 6 carbon atoms and may include formyl, acetyl, propionyl, butyryl, isobutyryl, valeryl, isovaleryl, pivaloyl, hexanoyl, and the like.

Suitable "lower alkylcarbamoyloxy" for $R^2$ may include methylcarbamoyloxy, ethylcarbamoyloxy, propylcarbamoyloxy, isopropylcarbamoyloxy, butylcarbamoyloxy, isobutylcarbamoyloxy, tert-butylcarbamoyloxy, pentylcarbamoyloxy, hexylcarbamoyloxy and the like.

Suitable protective group of the "protected hydroxy" for $R^3$ is a conventional protective group for hydroxy such as aryl (e.g. phenyl, tolyl, xylyl, cumenyl, naphthyl, o-chlorophenyl, etc.), ar(lower)alkyl (e.g. benzyl, p-methoxybenzyl, benzhydryl, trityl, trimethoxytrityl, etc.), lower alkanoyl as mentioned before, substituted lower alkanoyl (e.g. trifluoroacetyl, chloroacetyl, etc.), lower alkoxycarbonyl (e.g. methoxycarbonyl, trichloroethoxycarbonyl, tert-butoxycarbonyl, etc.), aroyl (e.g. benzoyl, toluoyl, xyloyl, naphtoyl, etc.), ar(lower)alkanoyl (e.g. phenylacetyl, phenylpropionyl, phenylbutyryl, etc.), aralkoxycarbonyl (e.g. benzyloxycarbonyl, etc.), and the like. Among these protective groups, more preferable ones are aryl and ar(lower)alkyl.

Suitable "lower alkoxy substituted with 2 or more hydroxy groups" for $R^4$ may include 2,3-dihydroxypropoxy, 1-hydroxymethyl-2-hydroxyethoxy, 2,3-,2,4- or 3,4-dihydroxybutoxy, 2,3,4-trihydroxybutoxy, di-, tri-, tetra- or penta-hydroxypentyloxy, di-, tri-, tetra-, penta- or hexahydroxyhexyloxy and the like. These hydroxy groups may be protected by protective groups as mentioned before and/or two adjacent hydroxy groups may be protected as a cyclic acetal (e.g. methyleneacetal, ethylideneacetal, benzylideneacetal, isopropylideneacetal, etc.), and the like. More preferable protective groups are lower alkanoyl, ar(lower)alkyl, aroyl and cyclic acetal as mentioned before.

The above "lower alkoxy" group for $R^4$ may be further substituted with lower alkoxy group(s) (e.g. methoxy, ethoxy, propoxy, isopropoxy, butoxy, pentyloxy, hexyloxy, etc.).

Suitable "lower alicyclic-oxy group substituted with 2 or more hydroxy groups" for $R^4$ may include 2,3-, 2,4- or 3,4-dihydroxycyclobutoxy, 2,3,4-trihydroxycyclobutoxy, di-, tri- or tetra-hydroxycyclopentyloxy, cis-, epi-, allo-, myo-, muco-, neo, scyllo- or chiro-inosityl, di-, tri-, tetra- or penta-hydroxycyclohexyloxy and the like. The hydroxy groups contained in these groups may be protected with protective groups as mentioned before.

The above "lower alicyclic-oxy group" may be further substituted with lower alkoxy group(s) as mentioned before.

The above "alicyclic-oxy group" for $R^4$ may contain an oxygen atom in the alicyclic ring.

Suitable "alicyclic group containing an oxygen atom therein" may include saccharose such as hexose (e.g. allose, altrose, galactose, glucose, gulose, idose, mannose, talose, etc.), pentose (e.g. arabinose, lyxose, ribose, xylose, etc.), tetrose (e.g. erythrose, threose, etc.), and the like.

The aforementioned "lower alkoxy" and "lower alicyclicoxy" groups for $R^4$ may further be substituted with an alicyclic-oxy group which has two or more hydroxy or protected hydroxy groups and may contain an oxygen atom as illustrated above.

Suitable pharmaceutically acceptable salts of the object compounds (I) are conventional non-toxic salts and may include an alkali metal salt (e.g. sodium salt, potassium salt, etc.), and hydrate and solvate thereof.

It is to be noted that the compounds (I) include all of the possible optical isomers due to the asymmetric carbon atom in the molecule of the compounds (I).

The object compound (I) and its salt can be prepared by the following processes.

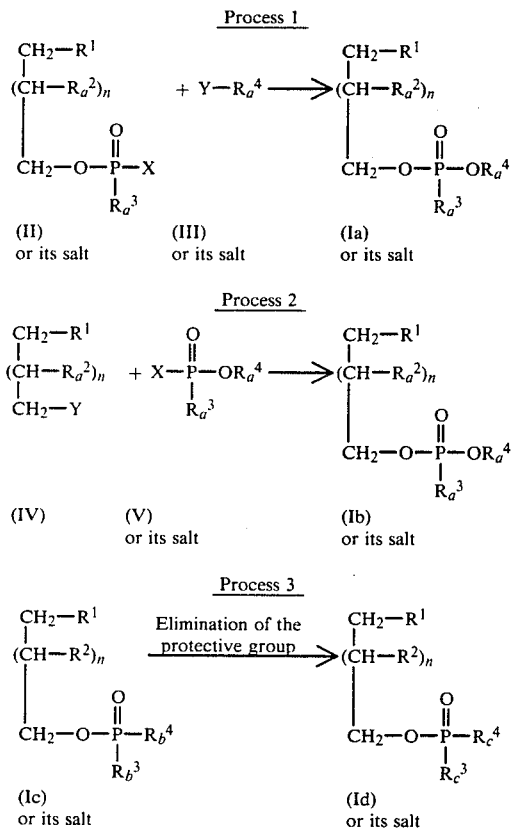

wherein $R^1$, $R^2$, and n are each as defined above;

$R_a^2$ is hydrogen, alkoxy, lower alkanoyloxy or lower alkylcarbamoyloxy;

$R_a^3$ is protected hydroxy;

$R_b^3$ and $R_b^4$ are each the same as $R^3$ and $R^4$ respectively, provided at least one protected hydroxy group is contained in $R_b^3$ and $R_b^4$;

$R_c^3$ and $R_c^4$ are each the same as $R^3$ and $R^4$ respectively, provided at least one hydroxy group is contained in $R^3$ and $R^4$;

$R_a^4$ is lower alkyl or lower alicyclic group which is substituted with 2 or more protected hydroxy groups and may be substituted with lower alkoxy or another alicyclic-oxy group having two or more protected hydroxy groups, in which the alicyclic ring may contain an oxygen atom; and X is halogen when Y is hydroxy, or X is silver-oxy when Y is halogen.

Suitable "halogen" for X and Y may include chlorine, bromine, iodine, fluorine.

Suitable "lower alkyl or lower alicyclic group" for $R_a^4$ is a group which forms "lower alkoxy or lower alicyclic-oxy group" for $R^4$ with an oxygen atom.

Suitable "protected hydroxy" for $R_a^3$ is the same as exemplified before for $R^3$.

The above processes are explained in detail in the followings.

PROCESS 1

The object compound (Ia) and its salt can be prepared by reacting a compound (II) or its salt with a compound (III) or its salt.

The suitable salts of the compound (Ia) and (II) can be referred to those as exemplified before for the compound (I).

The suitable salts of the compound (III) are the metal salts as exemplified before for the compound (I).

This reaction is usually carried out in a conventional solvent. Preferable solvent may be exemplified an aprotic solvent such as benzene, toluene, xylene, ether (e.g. diethyl ether, etc.), acetonitrile or any other solvent which does not adversely influence the reaction. The reaction temperature is not critical, and the reaction is usually carried out under warming or heating.

This reaction can also be carried out in the presence of an organic or inorganic base such as lower alkylamine (e.g. trimethylamine, triethylamine, etc.), pyridine, alkali metal acetate (e.g. sodium acetate, potassium acetate, etc.), alkali metal alkoxide (e.g. sodium methoxide, potassium tert-butoxide, etc.), metal hydroxide (e.g. sodium hydroxide, potassium hydroxide, etc.), and the like.

When the base is liquid, it can be used as a solvent. And further, this reaction can also be carried out in the presence of a condensing agent such as a carbodiimido compound (e.g. N,N'-dicyclohexylcarbodiimide, N-cyclohexyl-N'-morpholinoethylcarbodiimide, etc.), and the like, when both of X and Y are hydroxy.

PROCESS 2

The object compound (Ib) or its salt can be prepared by reacting a compound (IV) with a compound (V) or its salt.

The suitable salt of the compound (Ib) and (V) can be referred to those as exemplified before for the compound (I).

This reaction can be conducted according to substantially the same manner as that of Process 1.

PROCESS 3

The compound (Id) or its salt can be prepared by subjecting a compound (Ic) or its salt to an elimination reaction of the protective group in $R_b^3$ and/or $R_b^4$ and/or $R^2$.

Suitable salts of the compound (Ic) and (Id) can be referred to those as exemplified before for the compound (I).

Suitable method for the elimination reaction of the protective group(s) may include hydrogenolysis, hydrolysis, and the like depending on a kind of the protective group.

In case that the protective group to be eliminated is aryl and/or ar(lower)alkyl, the elimination reaction is preferably conducted by hydrogenolysis. This reaction can be carried out by conventional catalytic reduction, and suitable catalyst may include platinum catalyst (e.g. platinum oxide, platinum plate, platinum wire, platinum black, spongy platinum, etc.), palladium catalyst (e.g.

palladium on charcoal, palladium on barium sulfate, colloidal palladium, etc.), Raney Ni, and the like. The catalytic reduction is usually carried out in a conventional solvent such as water, methanol, ethanol, n-pentane, acetic acid or any other solvent which does not adversely influence the reaction. The reaction temperature is not critical, and the reaction is usually carried out at ambient temperature or under warming. The hydrogen pressure is not critical, and the reaction is usually carried out at 1 to 15 atms.

In case that the protective group to be eliminated is lower alkanoyl, substituted lower alkanoyl, lower alkoxycarbonyl, aroyl, ar(lower)alkanoyl, cyclic acetal, silyl and the like, the reaction can be carried out in the presence of a base or an acid.

Suitable base may include the ones as exemplified in the explanation of Process 1. In case a base such as alkali metal alkoxide or metal hydroxide is carefully used, lower alkanoyl, substituted lower alkanoyl, lower alkoxycarbonyl and ar(lower)alkanoyl are selectively eliminated. However, when a strong base such as metal hydroxide or alkalimetal alkoxide is excessively used, lower alkanoyl substituted lower alkanoyl, lower alkoxycarbonyl, ar(lower)alkanoyl and phosphate ester are eliminated.

Suitable acid may include an inorganic acid (e.g. hydrochloric acid, hydrobromic acid, sulfuric acid, etc.), an organic acid (e.g. formic acid, acetic acid, trifluoroacetic acid, p-toluenesulfonic acid, etc.), and the like. In case these acids are used in the hydrolysis, the cyclic acetal group is selectively eliminated.

The hydrolysis is usually carried out in a conventional solvent such as water, methanol, ethanol, tetrahydrofuran, dioxan or any other solvent which does not adversely influence the reaction. The reaction temperature is not critical and the reaction is usually carried out at ambient temperature or under warming.

The object compounds (I) obtained in the above Processes 1 and 2 can be isolated and purified in a conventional manner, for example, extraction, precipitation, fractional chromatography, fractional crystallization, recrystallization, and the like.

The object compounds (I) thus prepared can be transformed into optional pharmaceutically acceptable salt by a conventional method, if desired.

In case that the object compound (I) is obtained in a salt form, the resulting salt can be converted to its free form by means of an ion exchange resin or by treatment with an acid or a base, or the like.

Some of the starting compound (II) are novel, and can be prepared by processes as shown in the following Examples or processes chemically equivalent thereto.

The following pharmacological test data show that the object compounds (I) of the present invention exhibit high anti-tumor activity.

TEST METHOD

Groups of eight female BALB/c mice, aged 8-9, weeks and weighing 18.0-22.5 g were used.

Fibrosarcoma Meth A (hereinafter referred to as Meth A) was successively transferred every 7 days into BALB/c mice by intraperitoneal inoculation of the ascites cells thereof and the Meth A in the ascites cells as harvested 6 or 7 days after the inoculation was used as tumor cells.

Each of the BALB/c mice was inoculated intrapleurally with $5 \times 10^5$ Meth A cells in 0.1 ml Hanks solution.

Test compound was dissolved in phosphate buffer saline solution, and was injected into pleural cavity to each of the mice in doses of 100 μg/0.05 ml/mouse three times, i.e. before 14 days, after 1 hour and after 3 days of tumor implantation.

The control group was given with a vehicle alone in the same way.

The antitumor activity of the test compound was estimated by comparing mean survival time of the two groups.

T: Mean survival time of the medicated group
C: Mean survival time of the control group

TEST COMPOUND

Example 6-(3): Compound A

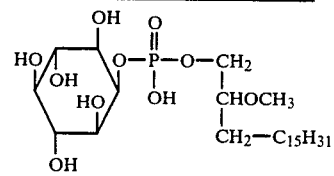

Example 11-(3): Compound B

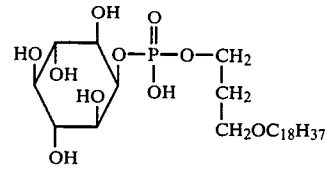

Example 10-(3): Compound C

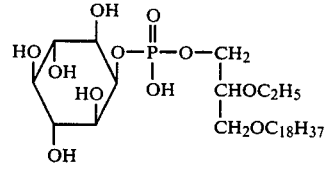

Example 15-(4): Compound D

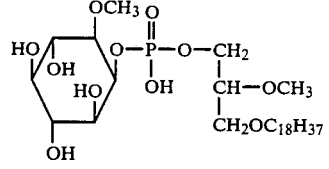

Example 8-(8): Compound E

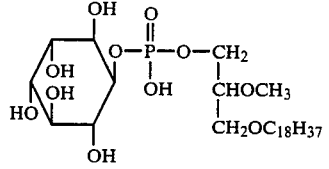

Example 7-(11): Compound F

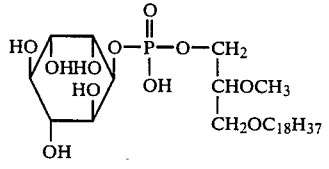

Example 9-(3): Compound G

-continued

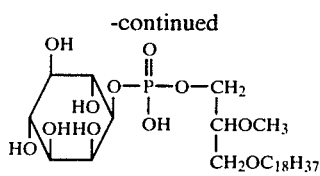

Example 18-(2): Compound H

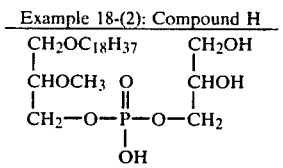

Reference compound: Compound I (rac)-1-O-Octadecyl-2-O-methylglycerol-3-phosphorylcholine which is described in British Pat. No. 1583661.

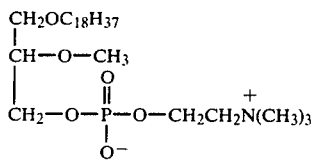

RESULTS

| Compound | Anti-tumor activity (%) *a |
|---|---|
| A | 412 |
| B | 325 |
| C | 383 |
| D | 308 |
| E | 442 |
| F | 475 |
| G | 358 |
| H | 308 |
| I | 302.8 |

*a: T/C × 100

As being apparent from the above test results, the object compound (I) of the present invention is useful as an antitumor agent.

The effective ingredient may usually be administered with a dose of 0.1 mg/kg to 500 mg/kg, 1 to 4 times a day in a preparations such as tablet, granule, powder, capsule, syrup, injection, suppository and the like. However, the above dosage may be increased or decreased according to the age, weight or conditions of the subject or the administering method.

The above mentioned pharmaceutical preparations can be prepared in a conventional manner by using conventional carriers and additives.

The present invention is illustrated by the following Examples in more detail.

EXAMPLE 1

(1) A mixture of silver 2-(1,3,4,5,6-penta-O-acetyl-DL-myo-inosityl) phenyl phosphate (11.9 g) and DL-2-O-methyl-1-O-octadecyl-glycerol 3-iodohydrin (8.5 g) in dry xylene (110 ml) was stirred for 3 hours under reflux in a dark. After cooling, the reaction mixture was filtered and the filtrate was evaporated under reduced pressure. The above obtained residue was dissolved in a minimum quantity of ethanol and treated with active carbon, and allowed to stand in a refrigerator for 24 hours. The resulting solid (11.3 g) was collected by filtration, and washed with ethanol, and subjected to column chromatography on silica gel (200 g, elution by chloroform) to give an oil (11.1 g) containing the object compound. The above obtained oil was crystallized and recrystallized from ethanol to give 9.09 g of DL-2-O-methyl-3-O-octadecyl-glyceryl 2-(1,3,4,5,6-penta-O-acetyl-DL-myo-inosityl) phenyl phosphate.

m.p. 67° to 68° C.

I.R. (Nujol): 1755 cm$^{-1}$.

(2) A solution of the above obtained compound of Example 1-(1)(8.86 g) in acetic acid (89 ml) was hydrogenated at 2.0 to 3.5 atms hydrogen pressure in the presence of platinum oxide (0.5 g) for 3 hours at ambient temperature. After removing the catalysts from the reaction mixture by filtration, the solvent was evaporated under reduced pressure.

The above obtained residue (12 g) was dissolved in ethanol (20 ml) and a solution of potassium acetate (1.08 g) in hot ethanol (10 ml) was added thereto. After cooling, the resultant solid was collected by filtration, washed with ethanol and hot acetone successively to give 8.3 g of potassium DL-2-O-methyl-3-O-octadecyl-glyceryl 2-(1,3,4,5,6-penta-O-acetyl-DL-myo-inosityl) phosphate.

I.R.(Nujol): 1760 cm$^{-1}$.

(3) To a solution of the above obtained compound of the Example 1-(2)(2.5 g) in methanol (50 ml) was added 28% sodium methoxide in methanol (5 ml).

After stirring for 10 minutes at ambient temperature, the resulting sodium salt of the object compound was collected by filtration, washed with methanol and dried. The above obtained sodium salt was dissolved in a mixture (30 ml) of chloroform and methanol (10:1), and passed through Dowex 50 resin (H+)(10 ml). The evaporation of the eluates gave 1.9 g of DL-2-O-methyl-3-O-octadecyl-glyceryl 2-(DL-myo-inosityl) phosphate as a crystal.

m.p. 153° to 154° C. (shrinking) (recrystallized from methanol).

I.R. (Nujol): 3300 cm$^{-1}$.

N.M.R.(100 MHz, CDCl$_3$—CD$_3$OD)ppm: 0.87 (3H,m), 1.28(32H, s), 3.5 (10H, m), 4.1–4.8 (6H, m).

Anal. Calcd. for C$_{28}$H$_{57}$O$_{11}$P.H$_2$O: C: 54.35, H: 9.61, Found: C: 54.73, H: 9.61.

EXAMPLE 2

(1) DL-2-O-Acetyl-3-O-octadecyl-glyceryl 2-(1,3,4,5,6-penta-O-acetyl-DL-myo-inosityl) phenyl phosphate (1.75S g) was obtained by reacting silver 2-(1,3,4,5,6-penta-O-acetyl-DL-myo-inosityl phenyl phosphate (2.63 g) with DL-2-O-acetyl-3-O-octadecyl-glycerol iodohydrin (2.0 g) according to a similar manner to that of Example 1-(1).

m.p. 40° to 45° C.

I.R.(Nujol): 1750, 1590,1290,1220,1045,1000,950 cm$^{-1}$.

N.M.R. (CDCl$_3$): 0.88(3H,m), 1.0–1.6(32H,m), 1.78(3H, s), 2.00(9H,s), 2.04(3H,s), 2.10(3H,s), 3.2–3.7(4H,m), 4.2–4.5(2H,m), 4.9–5.7(7H,m),7.30(5H,m).

(2) A solution of the above obtained compound of Example 2-(1)(1.72 g) in acetic acid (17 ml) was hydrogenated at 2.5 atms hydrogen pressure in the presence of platinum oxide (94 mg) for 3.5 hours at the ambient temperature. After removing the catalysts from the reaction mixture by filtration, the solvent was evaporated under reduced pressure and further the solvent was removed as the xylene and ethanol azeotrope successively.

The above obtained residue (1.60 g) was dissolved in dry methanol and a solution of 28% sodium methoxide in methanol (2.8 g) was added dropwise thereto at ambient temperature. After stirring for 0.5 hours at the same temperature, the resultant solid was collected by filtration, washed with methanol to give 1.15 g of sodium DL-3-O-octadecyl-glyceryl 2-(DL-myo-inosityl) phosphate as a colorless crystals.

I.R. (Nujol): 3300, 1220, 1050, 965, 720 cm$^{-1}$.

(3) The above object compound of Example 2-(2)(1.15 g) was dissolved in a solvent (120 ml, a mixture of chloroform: methanol: water, 3:2:15), and passed through Dowex 50 resin (H+)(13.8 ml). The eluates were evaporated and the residue was recrystallized from methanol to give 0.69 g of DL-3-O-octadecyl-glyceryl 2-(DL-myo-inosityl) phosphate.

m.p. 146° to 148° C.

I.R. (Nujol): 3300, 3250, 1215, 1120, 1050, 1040, 1010, 720 cm$^{-1}$.

N.M.R. (CD$_3$OD)ppm: 0.9 (3H, m), 1.0–1.7 (32H, m), 3.2–3.8 (10H, m), 3.8–4.2 (3H, m).

Anal. Calcd. for $C_{27}H_{55}O_{11}P \cdot H_2O$: C: 53.63, H: 9.50, Found: C: 54.14, H: 9.42.

EXAMPLE 3

(1) DL-2-O-methyl-3-O-hexadecyl-glyceryl 2-(1,3,4,5,6-penta-O-acetyl-DL-myo-inosityl) phenyl phosphate (2.23 g) was obtained by reacting silver 2-(1,3,4,5,6-penta-O-acetyl-DL-myo-inosityl) phenyl phosphate (2.97 g) with DL-2-O-methyl-3-O-hexadecyl-glycerol iodohydrin (2.0 g) according to a similar manner to that of Example 1-(1).

m.p. 56° to 59° C.

I.R. (Nujol): 1755, 1590, 1285, 1225, 1050, 1030, 1010, 1000, 955, 775 cm$^{-1}$.

N M.R. (CDCl$_3$)ppm: 0.89 (3H, m), 1.0–1.65 (28H, m), 1.79 (3H, s), 2.04 (9H, s), 2.10 (3H, s), 3.1–3.8 (5H, m), 3.48 (3H, s), 4.1–4.5 (2H, m), 4.9–5.8 (6H, m), 7.36 (5H, m).

(2) Sodium DL-2-O-methyl-3-O-hexadecyl-glyceryl 2-(DL-myo-inosityl) phosphate (1.08 g) was obtained by treating the above obtained compound of Example 3-(1)(2.20 g) with hydrogen in the presence of platinum oxide and followed by treating with sodium methoxide according to a similar manner to that of Example 2-(2).

I.R. (Nujol): 3350, 1650, 1205, 1055, 970, 720 cm$^{-1}$.

(3) DL-2-O-Methyl-3-O-hexadecylglyceryl 2-(DL-myo-inosityl) phosphate (0.43 g) was obtained by treating the above obtained compound of Example 3-(2) (1.08 g) with Dowex 50 (H+) according to a similar manner to that of Example 2-(3).

m.p. 152° to 153° C.

I.R. (Nujol): 3300, 1230, 1195, 1120, 1050, 1005, 720 cm$^{-1}$.

N.M.R. (CD$_3$OD)ppm: 0.9 (3H, m), 1.0–1.8 (28H, m), 3.1–3.7 (11H, m), 3.48 (3H, s), 4.0–4.3 (2H, m).

Anal. Calcd. for $C_{26}H_{53}O_{11}P \cdot \frac{1}{2}H_2O$: C: 53.69, H: 9.36, Found: C: 53.45, H: 9.39.

EXAMPLE 4

(1) DL-2-O-Methyl-3-O-tetradecyl-glyceryl 2-(1,3,4,5,6-penta-O-acetyl-DL-myo-inosityl) phenyl phosphate (1.32 g) was obtained by reacting silver 2-(1,3,4,5,6-penta-O-acetyl-DL-myo-inosityl) phenyl phosphate (2.81 g) with DL-2-O-methyl-3-O-tetradecyl-glycerol iodohydrin (1.77 g) according to a similar manner to that of Example 1-(1).

m.p. 58° to 59° C.

I.R. (Nujol): 1750, 1285, 1225, 1050, 1030, 1010, 1000, 950 cm$^{-1}$.

N.M.R. (CD$_3$OD)ppm: 0.87 (3H, m), 1.0–1.6 (24H, m), 1.75(3H, s), 2.00 ( 9H, s), 2.06 (3H, s), 3.1–3.7 (5H, m), 3.42(3H, s), 4.2–4.5(2H, m), 5.0–5.6 (6H, m), 7.30 (5H, m).

(2) Sodium DL-2-O-methyl-3-O-tetradecyl-glyceryl 2-(DL-myo-inosityl) phosphate (0.66 g) was obtained by treating the above obtained compound of Example 4-(1) (1.28 g) with hydrogen in the presence of platinum oxide and followed by treating with sodium methoxide according to a similar manner to that of Example 2-(2).

I.R. (Nujol): 3300, 1210, 1055, 965 cm$^{-1}$.

(3) DL-2-O-Methyl-3-O-tetradecyl-glyceryl 2-(DL-myo-inosityl) phosphate (0.47 g) was obtained by treating the above obtained compound of Example 4-(2) with Dowex 50(H+) according to a similar manner to that of Example 2-(3).

m.p. 151° to 152° C.

I.R. (Nujol): 3300, 1230, 1200, 1120, 1050, 1010, 720 cm$^{-1}$.

N.M.R. (CD$_3$OD)ppm: 0.9 (3H, m), 1.0–1.7 (24H, m), 3.1–3.8 (11H, m), 3.46 (3H, s), 4.0–4.3 (2H, m).

Anal. Calcd. for $C_{24}H_{49}O_{11}P \cdot H_2O$: C: 51.23, H: 9.14, Found: C: 51.74, H: 9.14.

EXAMPLE 5

(1) DL-2-Methoxy-3-octadecylsulfonylpropyl 2-(1,3,4, 5,6-penta-O-acetyl-DL-myo-inosityl) phenyl phosphate (1.88 g) was obtained by reacting silver 2-(1,3,4,5,6penta-O-acetyl-DL-myo-inosityl) phenyl phosphate (2.53 g) with DL-2-methoxy-3-octadecylsulfonyl-1-iodopropane (2.0 g) according to a similar manner to that of Example 1-(1).

m.p. 60° to 65° C.

I.R. (Nujol): 1755, 1590, 1280, 1250, 1220, 1135, 1115, 1040, 1020, 955 cm$^{-1}$.

N.M.R. (CDCl$_3$)ppm: 0.88 (3H, m), 1.0–1.6 (32H, m), 1.76 (3H, s), 2.04 (9H, s), 2.12 (3H, s), 2.9–3.3 (4H, m), 3.50 (3H, s), 3.9–4.6 (3H, m), 4.9–5.8 (6H, m), 7.36 (5H, m).

(2) Sodium DL-2-methoxy-3-octadecylsulfonylpropyl 2-(DL-myo-inosityl) phosphate (1.19 g) was obtained by subjecting the object compound of Example 5-(1)(1.85 g) with hydrogen in the presence of platinum oxide and followed by reacting sodium methoxide according to a similar manner to that of Example 2-(2).

(3) DL-2-Methoxy-3-octadecylsulfonylpropyl 2-(DL-myo-inosityl) phosphate (0.91 g) was obtained by treating the object compound of Example 5-(2)(1.19 g) with Dowex 50 (H+) according to a similar manner to that of Example 2-(3).

m.p. 149° to 151° C.

I.R. (Nujol): 3300, 1295, 1220, 1190, 1120, 1045, 1010, 720 cm$^{-1}$.

N.M.R. (CD$_3$OD)ppm: 0.9 (3H, m), 1.1–2.0 (32H, m), 3.0–3.8 (11H, m), 3.48 (3H, s), 4.1–4.4 (2H, m).

Anal. Calcd. for $C_{28}H_{57}O_{11}PS$: C: 51.83, H: 8.86, Found: C: 51.56, H: 9.01.

EXAMPLE 6

(1) DL-2-Methoxyoctadecyl 2-(1,3,4,5,6-penta-O-acetyl-DL-myo-inosityl) phenyl phosphate (1.20 g) was obtained as a waxy solid by reacting silver 2-(1,3, 4,5,6-penta-O-acetyl-DL-myo-inosityl) phenyl phosphate (2.80 g) with DL-2-methoxyoctadecyl iodide (1.76 g) according to a similar manner to that of Example 1-(1).

I.R. (Nujol): 1755, 1590, 1275, 1220, 1045, 1000, 950, 755 cm$^{-1}$.

N.M.R. (CDCl$_3$)ppm: 0.9 (3H, m), 1.0–1.6 (30H, m), 1.78 (3H, s), 2.02 (9H, s), 2.10 (3H, s), 3.2–3.6 (1H, m), 3.40 (3H, s), 4.0–4.3 (2H, m), 4.9–5.8 (6H, m), 7.36 (5H, m).

(2) Sodium DL-2-methoxyoctadecyl 2-(DL-myo-inosityl) phosphate (0.42g) was obtained by treating the above object compound of Example 6-(1)(1.15 g) with hydrogen in the presence of platinum oxide and followed by reacting with sodium methoxide according to a similar manner to that of Example 2-(2).

I.R. (Nujol): 3300, 1210, 1085, 1055, 965, 720 cm$^{-1}$.

(3) DL-2-Methoxyoctadecyl 2-(DL-myo-inosityl) phosphate (0.34 g) was obtained by treating the above object compound of Example 6-(2)(0.42g) with Dowex 50 (H$^+$) according to a similar manner to that of Example 2-(3).

m.p. 154°–155° C.

I.R. (Nujol): 3350, 1300, 1050, 1010, 720 cm$^{-1}$.

N.M.R. (CD$_3$OD)ppm: 0.9 (3H, m), 1.0–1.8 (30H, m), 3.1–3.8 (7H, m), 3.48 (3H, s), 4.0–4.3 (2H, m).

Anal. Calcd. for C$_{25}$H$_{51}$O$_{10}$P.H$_2$O: C: 53.56, H: 9.53, Found: C: 53.67, H: 9.44.

EXAMPLE 7

(1) To a stirred solution of 1,4,5,6-tetra-O-acetyl-DL-myo-inositol (3.48 g) in dry methylenechloride (52 ml) containing dry pyridine (1.6 g) was added dropwise a solution of trifluoromethanesulfonic anhydride (4.23 g) in dry methylenechloride (5 ml) at −15° C. over a period of 30 minutes. After stirring for another 30 minutes at the same temperature, the chilled mixture was washed with aqueous hydrochloric acid, aqueous sodium bicarbonate solution and water, dried, and evaporated under reduced pressure. The residue was crystallized from diethyl ether to give 4.0 g of 1,4,5,6-tetra-O-acetyl-3-O-trifluoromethanesulfonyl-DL-myo-inositol.

m.p. 133° to 135° C. (recrystallized from a mixture of ethyl acetate and n-hexane)

I.R. (Nujol): 3500, 1755, 1735(s), 1140 cm$^{-1}$.

Anal. Calcd. for C$_{15}$H$_{19}$O$_{12}$SF$_3$: C: 37.50, H: 3.99, S: 6.68, Found: C: 37.90, H: 3.94, S: 6.95.

(2) To a stirred solution of 1,4,5,6-tetra-O-acetyl-3-O-trifluoromethanesulfonyl-DL-myo-inositol (4.46 g) and p-toluenesulfonic acid (0.17 g) in a mixture of dry methylene-chloride (89 ml) and dry chloroform (22 ml) was added 2,3-dihydropyrane (3.90 g) in one portion under cooling at 5° to 10° C. After stirring for one hour at the same temperature, the mixture was washed with aqueous sodium bicarbonate and water, dried, and evaporated under reduced pressure. The residue was crystallized from n-hexane to yield 4.74 g of 1,4,5,6-tetra-O-acetyl-2-O-(2-tetrahydropyranyl)-3-O-trifluoromethanesulfonyl-DL-myo-inositol.

m.p. 130° to 131° C. (recrystallized from methanol).

I.R. (Nujol): 1750, 1145 cm$^{-1}$.

Anal. Calcd. for C$_{20}$H$_{27}$O$_{13}$SF$_3$: C: 42.55, H: 4.82, S: 5.68, Found: C: 42.16, H: 4.85, S: 5.78.

(3) A mixture of above obtained compound of Example 7-(2) (10.5 g) and sodium bicarbonate (1.56 g) in N,N-dimethylformamide (100 ml) and water (8 ml) was heated under stirring for 70 minutes at 115° to 120° C. The mixture was evaporated to dryness, and the residue was dissolved in chloroform (100 ml) and brine (50 ml). The organic layer was separated, dried, and evaporated under reduced pressure. The residue was subjected to column chromatography on silica gel (200 g, elution by chloroform and then 1% methanol in chloroform). The eluates which contain the object compounds were evaporated to give 7.67 g of a mixture of 2,3,4,5-tetra-O-acetyl-1-O-(2-tetrahydropyranyl)-DL-chiro-inositol and 2,3,4,6-tetra-O-acetyl-1-O-(2-tetrahydropyranyl)-DL-chiro-inositol as an oil, which was used in the following step (Example 7-(4)) without further purification.

(4) To a stirred mixture of the above obtained compounds of Example 7-(3)(7.67 g) in dry pyridine (15 ml) was added dropwise over a period of 20 minutes, a solution of acetyl chloride (1.82 g) in dry benzene (15 ml) under heating on a water bath. After stirring for 4 hours at room temperature, the mixture was poured into a mixrure of ethyl acetate (50 ml) and water (50 ml) under vigorous stirring. The organic layer was separated and the aqueous layer was extracted with ethyl acetate. The organic layer and extracts were combined, and washed with aqueous hydrochloric acid and water, dried, and evaporated to dryness. The residue was purified by column chromatography on silica gel (140 g, elution by chloroform). The eluates which containing the object compounds were evaporated and the residue was crystallized from diisopropyl ether to give 4.86 g of 2,3,4,5,6-penta-O-acetyl-1-O-(2-tetrahydropyranyl)-DL-chiro-inositol.

m.p. 158° to 161° C.

(5) A solution of the above obtained compound of Example 7-(4)(4.88 g) in a mixture of acetic acid (49 ml) and water (11 ml) was heated at 65° to 70° C. for 1.5 hours. The reaction mixture was evaporated to dryness and the residue was crystallized from diisopropyl ether to give 3.66 g of 2,3,4,5,6-penta-O-acetyl-DL-chiro-inositol.

m.p. 121° to 123° C.

I.R. (Nujol): 3520, 1750, 1740, 1720 cm$^{-1}$.

Anal. Calcd. for C$_{16}$H$_{22}$O$_{11}$: C: 49.23, H: 5.68, Found: C: 49.33, H: 5.81.

(6) To a stirred solution of 1,2,4-triazole (1.66 g) and triethylamine (2.42 g) in dry tetrahydrofuran (64 ml) was added dropwise during a period of 50 minutes, a solution of phenyl phosphorodichloridate (2.53 g) in dry tetrahydrofuran (8 ml) at 0° C. After stirring for another 50 minutes at the same temperature, the mixture was filtered. To the filtrate was added dropwise over a period of 23 minutes, a solution of 2,3,4,5,6-penta-O-acetyl-DL-chiro-inositol (3.12 g) in dry pyridine (40 ml) at ambient temperature. The mixture was stirred for 45 minutes at the same temperature and further stirred for 2.5 hours at 50° to 60° C. After cooling, the mixture was concentrated under reduced pressure and an aqueous solution of sodium bicarbonate was added thereto. After washing the solution with ethyl acetate, the aqueous layer was acidified with 10% aqueous hydrochloric acid and extracted with ethyl acetate. The extract was washed with water and dried over magnesium sulfate. The solvent was evaporated to give 2.82 g of 1-(2,3,4,5,6-penta-O-acetyl-DL-chiro-inosityl) phenyl phosphate as a waxy solid.

I.R. (Nujol): 1755, 1590, 1215, 1060, 1040, 960, 940 cm$^{-1}$.

N.M.R. (CDCl$_3$)ppm: 1.6–2.3 (15H, m), 4.7–5.7 (6H, m), 7.0–7.5 (5H, m), 8.4 (1H, br).

(7) To a solution of the above obtained compound of Example 7-(6)(2.77 g) in ethanol (8.5 ml) was added a solution of potassium acetate (0.50 g) in ethanol (8.5 ml) under stirring at ambient temperature. The mixture was stirred for 10 minutes at the same temperature and concentrated under reduced pressure. The residue was pulverized with n-hexane and collected by filtration to give white powder of potassium 1-(2,3,4,5,6-penta-O-acetyl-DL-chiro-inosityl) phenyl phosphate (3.12 g).

I.R. (Nujol): 3400, 1740, 1590, 1220, 1040, 950, 910, 820, 760, 730, 685 cm$^{-1}$.

(8) To a solution of the above obtained compound of Example 7-(7)(2.96 g) in water (3 ml) was added in one portion a solution of silver nitrate (0.86 g) in water (2 ml) at ambient temperature. The precipitates were filtered off and the filtrate was concentrated under reduced pressure. The residue was dissolved in chloroform, filtered and the filtrate was concentrated under reduced pressure. The residue was pulverized with diisopropyl ether and collected by filtration to give pale yellow powder of silver 1-(2,3,4,5,6-penta-O-acetyl-DL-chiro-inosityl) phenyl phosphate (2.36 g).

I.R. (Nujol): 1755, 1590, 1220, 1060, 920 cm$^{-1}$.

(9) DL-2-O-Methyl-3-O-octadecyl-glyceryl 1-(2,3,4,5,6-penta-O-acetyl-DL-chiro-inosityl) phenyl phosphate (1.48 g) was obtained as an oil by reacting the above obtained compound of Example 7-(8)(2.31 g) with 2-O-methyl-3-O-octadecyl-glycerol iodohydrin (1.66 g) according to a similar manner to that of Example 1-(1).

I.R. (film): 2920, 2850, 1755, 1590, 1280, 1210, 1040, 960, 755 cm$^{-1}$.

N.M.R. (CDCl$_3$)ppm: 0.9 (3H, m), 1.0–1.7 (32H, m), 1.8–2.25 (15H, m), 3.2–3.7 (8H, m), 4.1–4.4 (2H, m), 4.7–5.7 (6H, m), 7.1–7.5 (5H, m).

(10) Sodium DL-2-O-methyl-3-O-octadecyl-glyceryl 1-(DL-chiro-inosityl) phosphate (0.89 g) was obtained by treating the above obtained compound of Example 7-(9)(1.45 g) with hydrogen in the presence of platinum oxide and followed by reacting with sodium methoxide according to a similar manner to that of Example 2-(2).

I.R. (Nujol): 3300, 1215, 1090, 1065, 1020 cm$^{-1}$.

(11) DL-2-O-Methyl-3-O-octadecyl-glyceryl 1-(DL-chiro-inosityl) phosphate (0.57 g) was obtained by treating the above obtained compound of Example 7-(10)(0.89 g) with Dowex 50 (H+) according to a similar manner to that of Example 2-(3).

m.p. 147° to 148° C.

I.R. (Nujol): 3300, 1105, 1045, 1020 cm$^{-1}$.

N.M.R. (CD$_3$OD)ppm: 0.9 (3H, m), 1.1–1.7 (32H, m), 3.1–3.8 (11H, m), 3.46 (3H, s), 3.95–4.25 (2H, m).

Anal. Calcd. for C$_{28}$H$_{57}$O$_{11}$P.½H$_2$O: C: 55.15, H: 9.59, Found: C: 55.11, H: 9.76.

EXAMPLE 8

(1) 2,3,4,5,6-Penta-O-acetyl-1-O-trifluoromethanesulfonyl-DL-myo-inositol (10.05 g) was obtained by reacting the above obtained compound of Example 7-(1)(15.28 g) with acetyl chloride (3.26 g) according to a similar manner to that of Example 7-(4).

m.p. 163° to 164° C.

I.R. (Nujol): 1760, 1745, 1420, 1140 cm$^{-1}$.

(2) A solution of the above obtained compound of Example 8-(1)(7.23 g) in a mixture of phosphate buffer solution (14 ml, PH8.0, Na$_2$HPO$_4$-NaH$_2$PO$_4$, 0.1 Mol solution) and N,N-dimethylformamide (82 ml) was heated at 115° to 120° C. for 1.5 hours. The mixture was evaporated to dryness. The residue was dissolved in a mixture of brine (100 ml) and ethyl acetate (100 ml) under vigorous stirring. The organic layer was separated and the aqueous layer was extracted with ethyl acetate. The separated organic layer and the extracts were combined, washed with brine, dried, and evaporated. The residue was crystallized from diethyl ether to yield 2.99 g of 1,3,4,5,6-penta-O-acetyl-DL-chiro-inositol.

m.p. 170° to 172° C. (recrystallized from a mixture of ethyl acetate and n-hexane).

I.R. (Nujol): 3450, 1750 cm$^{-1}$.

Anal Calcd. for C$_{16}$H$_{22}$O$_{11}$: C: 49.23, H: 5.68, Found: C: 49.23, H: 5.76.

(3) 2-(1,3,4,5,6-Penta-O-acetyl-DL-chiro-inosityl) phenyl phosphate (2.76 g) was obtained by reacting the above obtained compound of Example 8-(2)(3.27 g) with phenyl phosphorodichloridate (2.65 g) and 1,2,4-triazole (1.73 g) according to a similar manner to that of Example 7-(6).

m.p. 171° to 175° C.

I.R. (Nujol): 1755, 1590, 1210, 1040, 960 cm$^{-1}$.

(4) Potassium 2-(1,3,4,5,6-penta-O-acetyl-DL-chiro-inosityl) phenyl phosphate (3.03 g) was obtained by reacting the above obtained compound of Example 8-(3) (2.73 g) with potassium acetate (0.49 g) according to a similar manner to that of Example 7-(7).

I.R. (Nujol): 3350, 1750, 1590, 1210, 1030, 900, 750 cm$^{-1}$.

(5) Silver 2-(1,3,4,5,6-penta-O-acetyl-DL-chiro-inosityl) phenyl phosphate (2.89 g) was obtained by reacting the above obtained compound of Example 8-(4)(3.0 g) with silver nitrate (0.88 g) according to a similar manner to that of Example 7-(8).

I.R. (Nujol): 3400, 1750, 1590, 1220, 1060, 930 cm$^{-1}$.

(6) DL-2-O-Methyl-3-O-octadecyl-glyceryl 2-(1,3,4,5,6-penta-O-acetyl-DL-chiro-inosityl) phenyl phosphate (1.76 g) was obtained as an oil by reacting the above obtained compound of Example 8-(5)(2.89 g) with DL-2-O-methyl-3-O-octadecyl-glycerol iodohydrin (2.07 g) according to a similar manner to that of Example 1-(1).

I.R. (film): 1755, 1590, 1490, 1370, 1215, 1060, 1035, 950, 760 cm$^{-1}$.

N.M.R. (CDCl$_3$)ppm: 0.86 (3H, m), 1.0–1.6 (32H, m), 1.6–2.24 (15H, m), 3.2–3.6 (8H, m), 4.0–4.3 (2H, m), 4.7–5.6 (6H, m), 7.0–7.44 (5H, m)

(7) Sodium DL-2-O-methyl-3-O-octadecyl glyceryl 2-(DL-chiro-inosityl) phosphate (0.93 g) was obtained by treating the above obJect compound of Example 8-(6)(1.68 g) with hydrogen in the presence of platinum oxide and followed by reacting with sodium methoxide according to a similar manner to that of Example 2-(2).

I.R. (Nujol): 3300, 1215, 1065, 1025 cm$^{-1}$.

(8) DL-2-O-Methyl-3-O-octadecyl-glyceryl 2-(DL-chiro-inosityl) phosphate (0.65 g) was obtained by treating the object compound of Example 8-(7)(0.93 g) with Dowex 50 (H+) resin according to a similar manner to that of Example 2-(3).

m.p. 144° to 145° C.

I.R. (Nujol): 3370, 1100, 1065, 1040 cm$^{-1}$.

N.M.R. (CD$_3$OD)ppm: 0.9 (3H, m), 1.0–1.7 (32H, m), 3.1–4.0 (11H, m), 3.48 (3H, s), 4.0–4.25 (2H, m).

Anal. Calcd. for C$_{28}$H$_{57}$O$_{11}$P.H$_2$O: C: 54.35, H: 9 61, Found: C: 54.60, H: 9.62.

EXAMPLE 9

(1) DL-2-O-Methyl-3-O-octadecyl-glyceryl 1-(2,3,4,5,6-penta-O-acetyl-DL-myo-inosityl) phenyl phosphate (1.72 g) was obtained as an oil by reacting silver 1-(2,3,4,5,6-penta-O-acetyl-DL-myo-inosityl) phenyl phosphate (3.27 g) with DL-2-O-methyl-3-O- octadecyl-glycerol iodohydrin (2.34 g) according to a similar manner to that of Example 1-(1).

I.R. (neat): 1750, 1590 cm$^{-1}$.

(2) A solution of the above object compound of Example 9-(1)(1.7 g) in acetic acid (17 ml) was hydrogenated at 2 to 3.5 atms hydrogen pressure in the presence of platinum oxide (100 mg) for 4 hours at ambient temperature. After removing the catalysts from the reaction mixture by filtration, the solvent was evaporated under reduced pressure, and further the solvent was removed as the xylene and ethanol azeotrope successively to give 1.51 g of DL-2-O-methyl-3-O-octadecyl-glyceryl 1-(2,3,4,5,6-penta-O-acetyl-DL-myo-inosityl) phosphate.

I.R. (Nujol): 1755 cm$^{-1}$.

(3) DL-2-O-Methyl-3-O-octadecyl-glyceryl 1-(DL-myo-inosityl) phosphate (0.72 g) was obtained by reacting the above obtained compound of Example 9-(2)(1.5 g) with sodium methoxide and followed by treating with Dowex 50 (H$^+$) resin according to a similar manner to that of Example 1-(3).

m.p. 157°–158° C. (shrinking at 126° C.).

I.R. (Nujol): 3570, 3300, 3180, 1465, 1390, 1120, 1060 cm$^{-1}$.

N.M.R. (100 MHz, CDCl$_3$—CD$_3$OD)ppm: 0.88 (3H, m), 1.25 (32H, s), 3.3–4.4 (16H, m).

Anal. Calcd. for C$_{28}$H$_{57}$O$_{11}$P.½H$_2$O: C: 55.16, H: 9.59, Found: C: 55.18, H: 9.84.

EXAMPLE 10

(1) DL-2-O-Ethyl-3-O-octadecyl-glyceryl 2-(1,3,4,5,6-penta-O-acetyl-DL-myo-inosityl) phenyl phosphate (3.5 g) was obtained by reacting silver 2-(1,3,4,5,6-penta-O-acetyl-DL-myo-inosityl) phenyl phosphate (4.25 g) with DL-2-O-ethyl-3-O-octadecyl-glycerol iodohydrin (3.14 g) according to a similar manner to that of Example 1-(1).

m.p. 36° to 40° C.

I.R. (Nujol): 1755, 1220, 1045 cm$^{-1}$.

(2) DL-2-O-Ethyl-3-O-octadecyl-glyceryl 2-(1,3,4,5,6-penta-O-acetyl-DL-myo-inosityl) phosphate (2.6 g) was obtained by reducing the above object compound of the Example 10-(1)(3.4 g) according to a similar manner to that of Example 9-(2).

m.p. 138° to 140° C.

I.R. (Nujol): 1760, 1225, 1110, 1040 cm$^{-1}$.

(3) DL-2-O-Ethyl-3-O-octadecyl-glyceryl 2-(DL-myo-inosityl) phosphate (1.6 g) was obtained by reacting the above obtained compound of Example 10-(2)(3.5 g) with sodium methoxide and followed by treating with Dowex 50 (H$^+$) resin according to a similar manner to that of Example 1-(3). m.p. 145° to 149° C.

I.R. (Nujol): 3340, 1110, 1050 cm$^{-1}$.

N.M.R. (CD$_3$OD—CDCl$_3$)ppm: 0.88 (3H, m), 1.00–1.73 (35H, m), 3.12–4.81 (15H, m).

Anal. Calcd. for C$_{29}$H$_{59}$O$_{11}$P.½H$_2$O: C: 55.84, H: 9.70, Found: C: 55.82, H: 9.93.

EXAMPLE 11

(1) 3-Octadecyloxypropyl 2-(1,3,4,5,6-penta-O-acetyl-DL-myo-inosityl) phenyl phosphate (3.7 g) was obtained by reacting silver 2-(1,3,4,5,6-penta-O-acetyl-DL-myo-inosityl) phenyl phosphate (2.89 g) with 1-iodo-3-octadecyloxypropane (1.94 g) according to a similar manner to that of Example 1-(1).

m.p. 55° to 64° C.

I.R. (Nujol): 3490, 1755, 1590, 1230, 1045 cm$^{-1}$.

(2) 3-Octadecyloxypropyl 2-(1,3,4,5,6-penta-O-acetyl-DL-myo-inosityl) phosphate (3.2 g) was obtained as a waxy solid by reducing the above object compound of Example 11-(1)(3.2 g) according to a similar manner to that of Example 9-(2).

I.R. (Nujol): 1760, 1220, 1040 cm$^{-1}$.

(3) 3-Octadecyloxypropyl 2-(DL-myo-inosityl) phosphate (2.1 g) was obtained by reacting the above obJect compound of Example 11-(2)(3.1 g) with sodium methoxide and followed by treating with Dowex 50(H$^+$) resin according to a similar manner to that of Example 1-(3).

m.p. 164° to 167° C.

I.R. (Nujol): 3300, 1240, 1120, 1040 cm$^{-1}$.

N.M.R. (CD$_3$OD—CDCl$_3$)ppm: 0.89 (3H, m), 1.04–1.77 (32H, m), 1.8–2.15 (2H, m), 3.14–4.88 (12H, m).

Anal. Calcd. for C$_{27}$H$_{55}$O$_{10}$P.¾H$_2$O: C: 55.51, H: 9.75, Found: C: 55.66, H: 9.78.

EXAMPLE 12

(1) DL-2,3-O-Dioctadecyl-glyceryl 2-(1,3,4,5,6penta-O-acetyl-DL-myo-inosityl) phenyl phosphate (3.77 g) was obtained by reacting silver 2-(1,3,4,5,6-penta-O-acetyl-DL-myo-inosityl) phenyl phosphate (2.68 g) with DL-2,3-O-dioctadecyl-glycerol iodohydrin (2.9 g) according to a similar manner to that of Example 1-(1).

m.p. 57° to 61° C.

I.R. (Nujol): 1750, 1230, 1050 cm$^{-1}$.

(2) DL-2,3-O-Dioctadecyl-glyceryl 2-(1,3,4,5,6-penta-O-acetyl-DL-myo-inosityl) phosphate (2.4 g) was obtained by reducing the above object compound of Example 12-(1)(3.7 g) according to a similar manner to that of Example 9-(2).

m.p. 127° to 129° C.

I.R. (Nujol): 1760, 1225, 1040 cm$^{-1}$.

(3) DL-2,3-O-Dioctadecyl-glyceryl 2-(DL-myo-inosityl) phosphate (1.68 g) was obtained by reacting the above object compound of Example 12-(2)(2.35 g) with sodium methoxide and followed by treating with Dowex 50(H$^+$) resin according to a similar manner to that of Example 1-(3).

m.p. 135° C.

I.R. (Nujol): 3330, 1220, 1110, 1045 cm$^{-1}$.

N.M.R. (CF$_3$CO$_2$H)ppm: 0.95 (6H, m), 1.11–2.20 (64H, m), 3.67–5.41 (15H, m).

Anal. Calcd. for C$_{45}$H$_{91}$O$_{11}$P: C: 64.41, H: 10.93, Found: C: 64.82, H: 11.08.

EXAMPLE 13

(1) DL-2-O-Methylcarbamoyl-3-O-octadecyl-glyceryl 2-(1,3,4,5,6-penta-O-acetyl-DL-myo-inosityl) phenyl phosphate (2.97 g) was obtained as an oil by reacting silver 2-(1,3,4,5,6-penta-O-acetyl-DL-myo-inosityl) phenyl phosphate (6.73 g) with 2-O-methylcarbamoyl-3-O-octadecyl-glyceryl chloride (3.33 g) according to a similar manner to that of Example 1-(1).

I.R. (Film): 3350, 2900, 2850, 1760, 1730, 1590, 1520, 1490, 1460 cm$^{-1}$.

(2) To a solution of the above obtained compound of Example 13-(1)(2.75 g) in 1,4 dioxane (41 ml) was added dropwise an aqueous 1N-sodium hydroxide solution (18 ml) during a period of 25 minutes at ambient temperature. After stirring for 4 hours at the same temperature, the reaction mixture was concentrated to ⅓ volume and allowed to cool in an ice bath. The resulting crystals were collected by filtration and then dissolved in hot water. The solution was acidified with 10% aqueous hydrochloric acid. After the mixture was allowed to stand in an ice bath, the resulting crystals were collected by filtration, washed with water, dried and recrystallized from ethanol to give 1.57 g of DL-2-O-methylcarbamoyl-3-O-octadecyl-glyceryl 2-(DL-myo-inosityl) phosphate.

m.p. 158° to 161° C.

I.R. (Nujol: 3300, 1700, 1540, 1255 cm$^{-1}$.

N.M.R. (CDCl$_3$—CD$_3$OD)ppm: 0.88 (3H, m), 1.06-1.73 (32H, m), 2.75 (3H, s), 3.13-4.36 (12H, m), 5.01 (1H, m).

Anal. Calcd. for C$_{29}$H$_{58}$NO$_{12}$P.½H$_2$O: C: 53.36, H: 9.11, N: 2.15, Found: C: 53.33, H: 9.57, N: 2.12.

EXAMPLE 14

(1) DL-2-Methoxy-3-octadecylthiopropyl 2-(1,3,4,5,6-penta-O-acetyl-DL-myo-inosityl) phenyl phosphate (2.64 g) was obtained by reacting silver 2-(1,3,4,5,6-penta-O-acetyl-DL-myo-inosityl) phenyl phosphate (2.24 g) with 3-octadecylthio-2-methoxypropyl 1-iodide (1.66 g) according to a similar manner to that of Example 1-(1).

m.p. 54° to 56° C.

I.R. (Nujol): 1755, 1590, 1290, 1220, 1050, 1030, 1010, 1000, 950 cm$^{-1}$.

N.M.R. (CDCl$_3$)ppm: 0.87 (3H, m), 1.03-1.6 (32H, m), 1.75 (3H, s), 2.00 (9H, s), 2.10 (3H, s), 2.35-2.80 (4H, m), 3.40 (3H, s), 3.35-3.70 (1H, m), 4.2-4.5 (2H, m), 4.90-5.70 (6H, m), 7.27 (5H, m).

(2) DL-2-Methoxy-3-octadecylthiopropyl 2-(DL-myo-inosityl) phosphate (0.58 g) was obtained by reacting the object compound of Example 14-(1)(2.20 g) with 1N-sodium hydroxide solution (15 ml) in a similar manner to that of the first half of Example 13-(2), and followed by treating with Dowex 50 (H+) resin according to a similar manner to that of Example 2-(3).

m.p. 185° C. (dec.).

I.R. (Nujol): 3330, 1210, 1090, 1050, 1000, 970, 860, 720 cm$^{-1}$.

N.M.R. (CDCl$_3$—CD$_3$OD)ppm: 0.9 (3H, m), 1.0-1.8 (32H,m), 2.3-3.0 (4H, m), 3.0-3.9 (7H, m), 3.45 (3H, s), 3.9-4.4 (2H, m).

Anal. Calcd. for C$_{28}$H$_{57}$O$_{10}$PS.2H$_2$O: C: 51.51, H: 9.41, Found: C: 50.96, H: 9.15.

EXAMPLE 15

(1) 2-(1-O-Methyl-3,4,5,6-tetra-O-benzyl-DL myo-inosityl) phenyl phosphate (5.8 g) was obtained as an oil by reacting 1-O-methyl-3,4,5,6-tetra-O-benzyl-DL-myo-inositol (5.54 g) with phenyl phosphorodichloridate according to a similar manner to that of Example 7-(6).

I.R. (CHCl$_3$): 1595 cm$^{-1}$.

(2) Silver 2-(1-O-methyl-3,4,5,6-tetra-O-benzyl-DL-myo-inosityl) phenyl phosphate (5.83 g) was obtained by reacting the above obtained compound of Example 15-(1)(5.7 g) with silver nitrate according to a similar manner to that of Example 7-(8).

m.p. 176°-186° C. (dec.).

I.R. (Nujol): 1590, 1490, 1455, 1370 cm$^{-1}$.

(3) DL-2-O-Methyl-3-O-octadecyl-glyceryl 2-(1-O-methyl-3,4,5,6-tetra-O-benzyl-DL-myo-inosityl) phenyl phosphate (4.66 g) was obtained as an oil by reacting the above obtained compound of Example 15-(2)(4.09 g) with DL-2-O-methyl-3-O-octadecyl-glycerol iodohydrin (2.34 g) according to a similar manner to that of Example 1-(1).

I.R. (neat): 3060, 3030, 2910, 2850, 1590, 1490, 1450 cm$^{-1}$.

(4) A solution of 4.6 g of the above object compound of Example 15-(3) in acetic acid (90 ml) was hydrogenated at 3.5 atms hydrogen pressure in the presence of 10% palladium on charcoal (4.6 g) and platinum oxide (0.5 g) for 8 hours. The catalysts were filtered off by filtration and the filtrate was evaporated to give 1.24 g of DL-2-O-methyl-3-O-octadecyl-glyceryl 2-(1-O-methyl-DL-myo-inosityl) phosphate.

m.p. 198° to 210° C. (shrinking at 110° C.).

I.R. (Nujol): 3300, 1460, 1370, 1210, 1090 cm$^{-1}$.

N.M.R. (CDCl$_3$—CD$_3$OD)ppm: 0.83 (3H, m), 1.25 (32H, s), 3.0-4.1 (18H, m), 4.7 (1H, m).

EXAMPLE 16

(1) 2-Octadecyloxyethyl 2-(1,3,4,5,6-penta-O-acetyl-DL-myo-inosityl) phenyl phosphate (8.1 g) was obtained by reacting silver 2-(1,3,4,5,6-penta-O-acetyl-DL-myo-inosityl) phenyl phosphate (8.66 g) with 2-octadecyloxyethyl iodide (4.68 g) according to a similar manner to that of Example 1-(1).

m.p. 61° to 64° C.

I.R. (Nujol): 1760, 1220 cm$^{-1}$.

(2) 2-Octadecyloxyethyl 2-(DL-myo-inosityl) phosphate (4.1 g) was obtained by treating the above object compound of Example 16-(1)(8.04 g) with sodium hydroxide and followed by treating with hydrochloric acid according to a similar manner to that of Example 13-(2).

m.p. 180° C. (recrystallized from ethanol).

I.R. (Nujol): 3300, 1230, 1120 cm$^{-1}$.

N.M.R. (CD$_3$OD)ppm: 0.99 (3H, m), 1.04-1.74 (32H, m), 3.00-4.32 (12H, m).

Anal. Calcd. for C$_{26}$H$_{53}$O$_{10}$P.H$_2$O: C: 54.34, H: 9.64, Found: C: 54.29, H: 9.28.

EXAMPLE 17

(1) To a solution of 1,2:5,6-di-O-isopropylidene-α-D-glucofuranose (3.12 g) in dry pyridine (31 ml) was added dropwise phenyl phosphorodichloridate (2.53 g) at 0° C. under stirring. After stirring for another 5 hours at 80° C., DL-2-O-methyl-3-O-octadecyl-glycerol (3.58 g) was added thereto in one portion, and the stirring was continued for 24 hours at 80° C. To a cooled reaction mixture, water (5 ml) was added dropwise, and the mixture was stirred for 30 minutes at ambient temperature. The solution was diluted with water, acidified with 10% hydrochloric acid, and extracted with ethyl acetate. The extracts were washed with 10% hydrochloric acid, water and brine respectively, dried, and evaporated. The above obtained residue was chromatographed on silica gel (75 g, elution by a mixture of chloroform: methanol, 50:1) to yield 4.95 g of DL-2-O-methyl-3-O-octadecyl-glyceryl 3-(1,2;5,6-di-O-isopropylidene-α-D-glucofuranosyl) phenyl phosphate as an oil.

I.R. (Neat): 2900, 2850, 1590, 1490 cm$^{-1}$.

(2) A solution of the above object compound of Example 17-(1)(4.9 g) in ethanol (49 ml) was hydrogenated at 2 atm. hydrogen pressure in the presence of platinum oxide (0.37 g) for 7 hours. After removing the catalysts from the reaction mixture by filtration and the filtrate was evaporated to dryness. The residue was dissolved in 80% aqueous acetic acid (90 ml) and stirred for 4 hours at 80° C.

The mixture was evaporated and the residue was crystallized from acetone to give crystals (1.80 g) containing the obJect compound. The above obtained crystals were purified by column chromatography to give 1.1 g of DL-2-O-methyl-3-O-octadecyl-glyceryl 3-($\alpha,\beta$-D-glucopyranosyl) phosphate.

m.p. 160° C. (dec.)

I.R. (Nujol): 3300, 1375, 1205 cm$^{-1}$.

N M.R. (100 MHz, CDCl$_3$—CD$_3$OD)ppm: 0.89 (3H, m), 1.30 (32H, s), 3.3–4.4 and 5.3 (18H, m).

Anal. Calcd for C$_{28}$H$_{57}$O$_{11}$P.2H$_2$O: C: 52.79, H: 9.65, Found: C: 52.14, H: 9.36.

EXAMPLE 18

(1) DL-2,3-O-Isopropylidene-glyceryl DL-2-O-methyl-3-O-octadecyl-glyceryl phenyl phosphate (2.25 g) was obtained as an oil by reacting DL-2-O-methyl-3-O-octadecyl-glycerol (1.79 g) with phenyl phosphoro dichloridate (1.16 g) and DL-2,3-O-isopropylidene glycerol (3.30 g) according to a similar manner to that of Example 17-(1).

I.R. (Neat): 1590, 1490, 1460 cm$^{-1}$.

(2) DL-1-Glyceryl DL-2-O-methyl-3-O-octadecyl-glyceryl phosphate (0.65 g) was obtained from the above object compound of Example 18-(1)(2.2 g) according to a similar manner to that of Example 17-(2).

m.p. 170°–173° C. (shrinking at 65° C.).

I.R. (Nujol): 3300, 1420, 1380, 1220 cm$^{-1}$.

N.M.R. (100 MHz, CDCl$_3$—D$_2$O)ppm: 0.88 (3H, m), 1.26 (32H, s), 3.3–4.0 (13H, m), 4.58 (2H, m).

Anal Calcd. for C$_{25}$H$_{53}$O$_8$P.2H$_2$O: C: 54.72, H: 9.74, Found: C: 54.99, H: 10.08.

EXAMPLE 19

(1) Silver DL-2-O-methyl-3-O-octadecyl-glyceryl phenyl phosphate (10.66 g) was obtained by reacting DL-2-O-methyl-3-O-octadecyl-glyceryl phenyl phosphate (15.0 g) with potassium acetate and followed by reacting with silver nitrate according to similar manners to those of Example 7-(7) and Example 7-(8).

m.p. 65° to 67° C.

I.R. (Nujol): 1590, 1490 cm$^{-1}$.

(2) DL-2-O-Methyl-3-O-octadecyl-glyceryl phenyl 2,3,4-tri-O-benzoyl-$\beta$-D-ribo-pyranosyl phosphate (3.62 g) was obtained by reacting the above obtained compound of Example 19-(1)(2.93 g) with 2,3,4-tri-O-benzoyl-$\beta$-D-ribo-pyranosyl bromide (2.1 g) according to a similar manner to that of Example 1-(1).

I.R. (Nujol): 1720 cm$^{-1}$.

(3) DL-2-O-Methyl-3-O-octadecyl-glyceryl 2,3,4-tri-O-benzoyl-$\beta$-D-ribo-pyranosyl phosphate (1.56 g) was obtained by reducing the above object compound of Example 19-(2)(3.62 g) in ethanol according to a similar manner to that of Example 9-(2).

I.R. (Nujol): 3450, 1735, 1450, 1380, 1245, 1125 cm$^{-1}$.

(4) DL-2-O-Methyl-3-O-octadecyl-glyceryl $\beta$-D-ribo-pyranosyl phosphate (0.17 g) was obtained by reacting the above object compound of Example 19-(3)(1.54 g) with sodium methoxide and followed by treating with Dowex 50(H$^+$) resin according to a similar manner to that of Example 1-(3).

m.p. 90° to 92° C.

I.R. (Nujol): 3350, 1375, 1060, 940 cm$^{-1}$.

N.M.R. (100 MHz, CDCl$_3$—CD$_3$OD)ppm: 0.90 (3H, m), 1.32 (32H, s), 3.3–4.5 (6H, m).

Anal. Calcd for C$_{27}$H$_{55}$O$_{10}$P.H$_2$O: C: 55.07, H: 9.76, Found: C: 55.30, H: 10.01.

EXAMPLE 20

(1) 1-O-(1,2,3,4-Tetra-O-acetyl-$\beta$-D-glucopyranos-6-yl)-2,3,4-tri-O-acetyl-$\beta$-D-glucopyranos-6-yl phenyl phosphate (4.79 g) was obtained by reacting 1-O-(1,2,3,4-tetra-O-acetyl-$\beta$-D-glucopyranos-6-yl)-2,3,4-tri-O-acetyl-$\beta$-D-glucopyranose (4.40 g) with phenyl phosphorodichloridate (2.17 g) according to a similar manner to that of Example 7-(6).

m.p. 129° to 135° C.

I.R. (Nujol): 3470, 1750, 1590, 1210, 1070, 1035, 775 cm$^{-1}$.

N.M.R. (CDCl$_3$/D$_2$O)ppm: 1.9–2.3 (21H, m), 3.5–5.3 (13H, m), 5.6–5.9 (1H, m), 6.50 (1H, br), 7.1–7.5 (5H, m).

(2) Potassium 1-O-(1,2,3,4-tetra-O-acetyl-$\beta$-D-glucopyranos-6-yl)-2,3,4-tri-O-acetyl-$\beta$-D-glucopyranos-6-yl phenyl phosphate (5.00 g) was obtained by treating the above obtained compound of Example 20-(1)(4.88 g) with potassium acetate (0.60 g) according to a similar manner to that of Example 7-(7).

I.R. (Nujol): 1750, 1590, 1245, 1220, 1075, 1040 cm$^{-1}$.

(3) Silver 1-O-(1,2,3,4-tetra-O-acetyl-$\beta$-D-glucopyranos-6-yl)-2,3,4-tri-O-acetyl-$\beta$-D-glucopyranos-6-yl phenyl phosphate (3.22 g) was obtained by reacting the above obtained compound of Example 20-(2)(4.99 g) with silver nitrate (1.02 g) according to a similar manner to that of Example 7-(8).

I.R. (Nujol): 3450, 1750, 1590, 1220, 1075, 1040 cm$^{-1}$.

(4) 1-O-(1,2,3,4-Tetra-O-acetyl-$\beta$-D-glucopyranos-6-yl)-2,3,4-tri-O-acetyl-$\beta$-D-glucopyranos-6-yl DL-2-O-methyl-3-O-octadecylglyceryl phenyl phosphate (2.4 g) was obtained as an oil by reacting the above object compound of Example 20-(3)(5.05 g) with DL-2-O-methyl-3-O-octadecyl-glycerol iodohydrin (2.63 g) according to a similar manner to that of Example 1-(1).

I.R. (Film): 1750, 1590, 1490, 1365, 1205, 1035 cm$^{-1}$.

N.M.R. (CDCl$_3$)ppm: 0.9 (3H, m), 1.0–1.7 (32H, m), 1.7–2.2 (21H, m), 3.42 (3H, s), 3.2–4.6 (14H, m), 4.7–5.8 (8H, m), 7.0–7.4 (5H, m).

(5) 1-O-(1,2,3,4-Tetra-O-acetyl-$\beta$-D-glucopyranos-6-yl)-2,3,4-tri-O-acetyl-B-D-glucopyranos-6-yl DL-2-O-methyl-3-O-octadecyl-glyceryl phosphate (2.39 g) was obtained as an oil by hydrogenating the above object compound of Example 20-(4)(2.40 g) according to a similar manner to that of Example 9-(2).

I.R. (Film): 3400, 1750, 1365, 1240, 1210, 1035, 755 cm$^{-1}$.

(6) Sodium 1-O-($\beta$-D-6-glucopyranosyl)-$\beta$-D-6-glucopyranosyl-DL-2-O-methyl-3-O-octadecyl-glyceryl phosphate (0.79 g) was obtained by treating the above object compound of the Example 20-(5)(2.35 g) with sodium methoxide according to a similar manner to that of the first half of the Example 1-(3).

I.R. (Nujol): 3300, 1645, 1210, 1080, 1050, 1025 cm$^{-1}$.

(7) 1-O-($\beta$-D-6-Glucopyranosyl)-$\beta$-D-6-glucopyranosyl DL-2-O-methyl-3-O-octadecyl-glyceryl phosphate (0.59 g) was obtained by treating the above object compound of the Example 20-(6)(1.45 g) with Dowex 50 (H$^+$) resin according to a similar manner to that of Example 2-(3).

m.p. 175° C. (dec.).

I.R. (Nujol): 3350, 1220, 1080, 1050 cm$^{-1}$.

N.M.R. (D$_2$O)ppm: 0.9 (3H, m), 1.32 (32H, m), 3.50 (3H, s), 3.2–4.4 (21H, m).

Anal. Calcd. for C$_{34}$H$_{67}$O$_{16}$P.3H$_2$O: C: 49.99, H: 9.01, Found: C: 49.73, H: 8.23.

What is claimed is:

1. A compound of the formula:

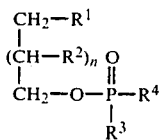

wherein
- $R^1$ is higher alkyl or higher alkoxy;
- $R^2$ is hydrogen, hydroxy or lower alkoxy;
- n is 0 or 1;
- $R^3$ is hydroxy; and
- $R^4$ is lower alkoxy or lower alicyclic-oxy group which is substituted with 2 or more hydroxy groups, and may be substituted with lower alkoxy;

or a pharmaceutically acceptable salt thereof.

2. A method for treating fibrosarcoma Meth A which comprises administering a pharmaceutically effective amount of the compound of claim 1 to a subject in need of said treatment.

3. A pharmaceutical composition for treating fibrosarcoma Meth A comprising an effective amount of the compound of claim 1 and a pharmaceutically acceptable carrier or excipient.

4. A compound according to claim 1, wherein $R^1$ is higher alkoxy, $R^2$ is lower alkoxy and n is 1.

5. The compound according to claim 4, which is DL-2-O-ethyl-3-O-octadecyl-glyceryl 2-(DL-myo-inosityl) phosphate.

6. The compound according to claim 4, which is DL-2-O-methyl-3-O-octadecyl-glyceryl 1-(DL-chiro-inosityl) phosphate.

7. A compound according to claim 1, wherein $R^1$ is higher alkoxy, $R^2$ is hydroxy and n is 1.

8. A compound according to claim 1, wherein $R^1$ is higher alkoxy and n is 0.

9. A compound according to claim 1, wherein $R^1$ is higher alkyl, $R^2$ is lower alkoxy and n is 1.

10. A compound according to claim 1, wherein $R^1$ is higher alkoxy, $R^2$ is hydrogen and n is 1.

* * * * *